United States Patent
Panser et al.

(10) Patent No.: US 8,257,415 B2
(45) Date of Patent: *Sep. 4, 2012

(54) WARMING DEVICE

(75) Inventors: Carol J. Panser, St. Louis Park, MN (US); Thomas P. Anderson, Savage, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/200,966

(22) Filed: Oct. 5, 2011

(65) Prior Publication Data

US 2012/0022623 A1    Jan. 26, 2012

Related U.S. Application Data

(63) Continuation of application No. 12/925,445, filed on Oct. 21, 2010, now Pat. No. 8,070,787, which is a continuation of application No. 11/492,425, filed on Jul. 25, 2006, now Pat. No. 7,846,192.

(51) Int. Cl.
    A61F 7/00        (2006.01)
(52) U.S. Cl. .......................... 607/104; 607/107
(58) Field of Classification Search .................. 607/104, 607/108, 107
    See application file for complete search history.

(56) References Cited

U.S. PATENT DOCUMENTS

| | | | |
|---|---|---|---|
| 2,512,559 A | 6/1950 | Williams | 5/347 |
| 2,573,414 A | 10/1951 | Dunn | 128/144 |
| 2,826,758 A | 3/1958 | Kahn | 2/61 |
| 3,468,299 A | 9/1969 | D'Amato | 126/204 |
| 3,610,323 A | 10/1971 | Troyer | 165/46 |
| 3,757,366 A | 9/1973 | Sacher | 5/347 |
| 3,855,635 A | 12/1974 | Ramirez | 2/114 |
| 3,911,499 A | 10/1975 | Benevento et al. | 2/114 |
| 3,950,789 A | 4/1976 | Konz et al. | 2/93 |
| 4,055,173 A | 10/1977 | Knab | 128/139 |
| 4,146,933 A | 4/1979 | Jenkins et al. | 2/2 |
| 4,369,528 A | 1/1983 | Vest et al. | 2/69 |
| 4,494,248 A | 1/1985 | Holder | 2/69 |
| 4,524,463 A | 6/1985 | Ogden | 2/105 |
| 4,558,468 A | 12/1985 | Landry et al. | 2/51 |
| 4,578,825 A | 4/1986 | Vote | 2/114 |
| 4,587,671 A | 5/1986 | Rodriguez et al. | 2/69 |
| 4,651,727 A | 3/1987 | Howorth | 128/201.3 |
| 4,653,120 A | 3/1987 | Leaf | 2/114 |

(Continued)

FOREIGN PATENT DOCUMENTS

EP    2043571 B1    1/2012

(Continued)

OTHER PUBLICATIONS

P.O. Fanger, Thermal Comfort: Analysis and Applications in Environmental Engineering, Danish Technical Press, 1970, pp. 5-67.

(Continued)

*Primary Examiner* — Roy Gibson
*Assistant Examiner* — Kaitlyn Smith
(74) *Attorney, Agent, or Firm* — Adam M. Bramwell; Terrance A. Meador

(57) ABSTRACT

A warming device includes a clinical garment having an inside surface supporting a convective apparatus with an inflatable dog-bone shaped section framed by an outline section.

16 Claims, 7 Drawing Sheets

U.S. PATENT DOCUMENTS

| | | | | |
|---|---|---|---|---|
| 4,696,066 | A | 9/1987 | Ball et al. | 2/272 |
| 4,718,124 | A | 1/1988 | Sawicki et al. | 2/114 |
| 4,787,101 | A | 11/1988 | Feinberg | 2/105 |
| 4,914,752 | A | 4/1990 | Hinson et al. | 2/2 |
| 4,964,282 | A | 10/1990 | Wagner | 62/259.3 |
| 5,062,424 | A * | 11/1991 | Hooker | 128/897 |
| 5,190,031 | A | 3/1993 | Guibert et al. | 128/399 |
| 5,255,390 | A | 10/1993 | Gross et al. | |
| 5,304,213 | A | 4/1994 | Berke et al. | 607/104 |
| 5,360,439 | A | 11/1994 | Dickerhoff et al. | 607/104 |
| 5,367,710 | A | 11/1994 | Karmin | 2/114 |
| 5,411,541 | A | 5/1995 | Bell et al. | 607/104 |
| 5,443,488 | A | 8/1995 | Namenye et al. | 607/104 |
| 5,572,742 | A | 11/1996 | McFadden | 2/114 |
| 5,575,006 | A | 11/1996 | Wolfe | 2/114 |
| 5,611,087 | A | 3/1997 | Adkins | 2/114 |
| 5,620,482 | A | 4/1997 | Augustine et al. | 607/107 |
| 5,675,848 | A | 10/1997 | Kappel | 5/482 |
| 5,697,963 | A | 12/1997 | Augustine | 607/108 |
| 5,733,318 | A | 3/1998 | Augustine | 607/104 |
| 5,749,109 | A | 5/1998 | Kappel | 5/423 |
| 5,785,716 | A | 7/1998 | Bayron | 607/108 |
| 5,891,187 | A | 4/1999 | Winthrop et al. | 607/96 |
| 5,946,722 | A | 9/1999 | Trautmann | 2/83 |
| 5,970,519 | A | 10/1999 | Weber | 2/81 |
| 5,974,605 | A | 11/1999 | Dickerhoff et al. | 5/421 |
| 6,049,907 | A | 4/2000 | Palomo | 2/51 |
| 6,154,883 | A | 12/2000 | Spann et al. | 2/69 |
| 6,156,058 | A | 12/2000 | Kappel et al. | 607/107 |
| 6,203,567 | B1 | 3/2001 | Augustine | 607/104 |
| 6,216,270 | B1 | 4/2001 | Moquin et al. | 2/69 |
| 6,235,659 | B1 | 5/2001 | McAmish et al. | 442/79 |
| 6,378,136 | B2 | 4/2002 | Matsushita | 2/114 |
| 6,484,321 | B1 | 11/2002 | Shamam | 2/114 |
| 6,511,501 | B1 | 1/2003 | Augustine et al. | 607/96 |
| 6,524,332 | B1 | 2/2003 | Augustine et al. | 607/107 |
| 6,551,347 | B1 | 4/2003 | Elkins | 607/104 |
| 6,571,574 | B1 | 6/2003 | Blackstone | 62/420 |
| 6,596,019 | B2 | 7/2003 | Turner et al. | 607/108 |
| 6,647,552 | B1 | 11/2003 | Hogan | 2/114 |
| 6,694,522 | B1 | 2/2004 | Neal | 2/114 |
| 6,792,622 | B2 | 9/2004 | Graves | 2/114 |
| 6,799,332 | B2 | 10/2004 | Hatton | 2/114 |
| 6,820,622 | B1 | 11/2004 | Teves et al. | 128/849 |
| 6,851,125 | B2 | 2/2005 | Fujikawa et al. | 2/51 |
| 6,876,884 | B2 * | 4/2005 | Hansen et al. | 607/98 |
| 7,001,416 | B2 | 2/2006 | Augustine et al. | 607/104 |
| 7,226,454 | B2 | 6/2007 | Albrecht et al. | 607/104 |
| 7,276,076 | B2 | 10/2007 | Bieberich | 607/108 |
| 7,364,584 | B2 | 4/2008 | Anderson | 607/108 |
| 7,470,280 | B2 | 12/2008 | Bieberich | 607/104 |
| 2003/0126668 | A1 * | 7/2003 | Scroggins | 2/114 |
| 2005/0015127 | A1 * | 1/2005 | Bieberich | 607/108 |
| 2005/0143796 | A1 * | 6/2005 | Augustine et al. | 607/104 |
| 2006/0047332 | A1 * | 3/2006 | Malmberg et al. | 607/104 |
| 2006/0122671 | A1 * | 6/2006 | Albrecht et al. | 607/104 |
| 2006/0122672 | A1 * | 6/2006 | Anderson | 607/104 |
| 2006/0147320 | A1 * | 7/2006 | Hansen et al. | 417/313 |
| 2006/0184216 | A1 | 8/2006 | Van Duren | 607/104 |
| 2006/0184217 | A1 * | 8/2006 | Van Duren | 607/104 |
| 2006/0184218 | A1 * | 8/2006 | Bieberich | 607/104 |
| 2006/0259104 | A1 * | 11/2006 | Panser et al. | 607/104 |
| 2007/0093882 | A1 * | 4/2007 | Anderson et al. | 607/104 |
| 2007/0093883 | A1 | 4/2007 | Anderson et al. | 607/104 |
| 2007/0093884 | A1 * | 4/2007 | Anderson et al. | 607/104 |
| 2007/0093885 | A1 * | 4/2007 | Anderson et al. | 607/104 |
| 2007/0239239 | A1 * | 10/2007 | Albrecht et al. | 607/96 |
| 2008/0027521 | A1 * | 1/2008 | Bieberich | 607/96 |
| 2008/0027522 | A1 * | 1/2008 | Bieberich | 607/104 |
| 2008/0125840 | A1 * | 5/2008 | Anderson | 607/104 |
| 2008/0177361 | A1 * | 7/2008 | Anderson | 607/108 |
| 2009/0062891 | A1 * | 3/2009 | Bieberich | 607/104 |
| 2009/0149931 | A9 * | 6/2009 | Anderson | 607/104 |
| 2009/0228083 | A1 * | 9/2009 | Anderson et al. | 607/107 |

FOREIGN PATENT DOCUMENTS

| | | |
|---|---|---|
| FR | 821150 | 11/1937 |
| GB | 475811 | 11/1937 |
| GB | 1 462 033 | 1/1997 |
| WO | WO 97/14381 A1 | 4/1997 |
| WO | WO 98/48652 A1 | 11/1998 |
| WO | WO 00/62726 A1 | 10/2000 |
| WO | WO 03/086500 A2 | 10/2003 |
| WO | WO 03/106897 A3 | 12/2003 |
| WO | WO 2004/004500 A1 | 1/2004 |
| WO | WO 2008/013603 A1 | 1/2008 |

OTHER PUBLICATIONS

C.B. Mahony & J. Odom, Maintaining intraoperative normothermia: A meta-analysis of outcomes with costs. *AANA Journal*. Apr. 1999. v. 67, No. 2:155-164.

Porta-Chill—The Portable Air-Chiller—Brochure, http://www.portachil.com/, Dec. 3, 2022.

International Search Report & Written Opinion in PCT/US2007/013073, mailed Nov. 9, 2007.

EPO Examination Report mailed Sep. 3, 2009 in EP 07795671.2, EP Regional Phase of PCT/US2007/013073 (published as WO/2008/013603).

Response to Examination Report in EP 07795671.2, submitted Mar. 26, 2010.

* cited by examiner

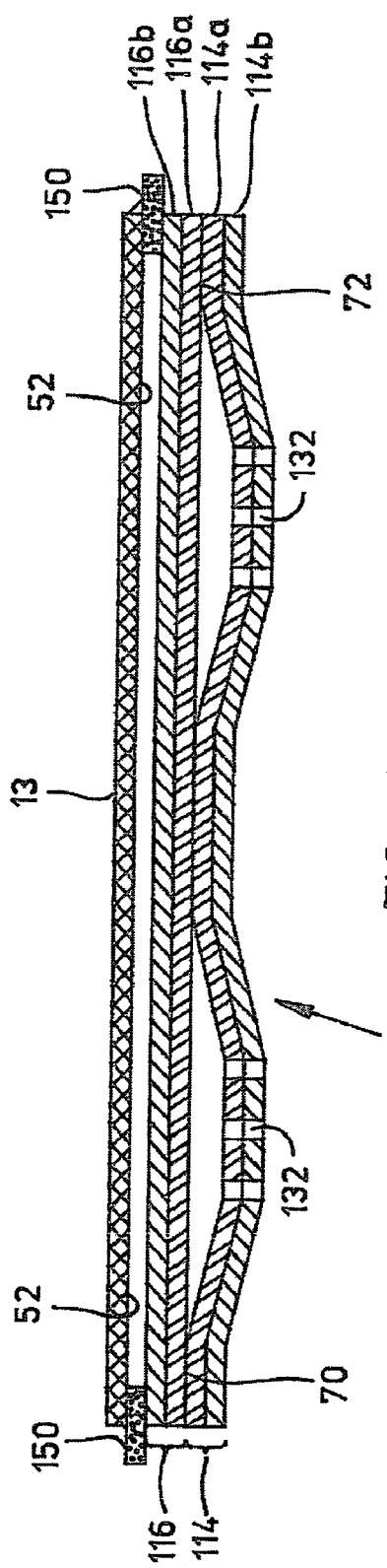
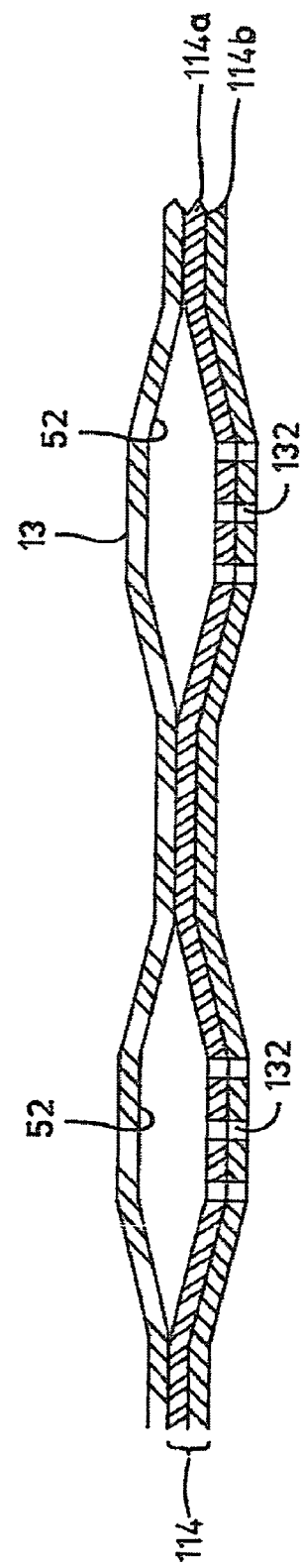

WARMING DEVICE

PRIORITY

This is a continuation of U.S. patent application Ser. No. 12/925,445, filed Oct. 21, 2010, now U.S. Pat. No. 8,070,787, which is a continuation of U.S. patent application Ser. No. 11/492,425, filed Jul. 25, 2006, now U.S. Pat. No. 7,846,192

RELATED APPLICATIONS

This application contains subject matter related to the subject matter of the following patent applications, all commonly owned herewith:

Patent Cooperation Treaty (PCT) Application No. PCT/US2003/011128, filed Apr. 10, 2003, titled "Patient Comfort Apparatus and System", and published on Oct. 23, 2003 under Publication No. WO 2003/086500;

PCT Application No. PCT/US2005/025355, filed Jul. 18, 2005, titled "Perioperative Warming Device", and published on Feb. 23, 2006 under Publication No. WO 2006/020170;

PCT Application No. PCT/US2005/043968, filed Dec. 6, 2005, titled "Warming Device with Varied Permeability", and published on Jun. 15, 2006 under Publication No. WO 2006/062910;

PCT Application No. PCT/US2005/044214, filed Dec. 6, 2005, titled "Warming Device", and published on Jun. 15, 2006 under Publication No. WO 2006/063027;

PCT Application No. PCT/US2006/004644, filed Feb. 9, 2006, titled "Warming Device for Perioperative Use", and published on Aug. 17, 2006 under Publication No. WO2006/086587;

PCT Application No. PCT/US/2006/41028, filed Oct. 19, 2006, titled "Multifunction Warming Device for Perioperative Use", and published on Apr. 26, 2007 under Publication No. WO2007/047917;

PCT Application No. PCT/US2007/013073, filed Jun. 1, 2007, titled "Warming Device", and published Jan. 31, 2008 under Publication No. WO 2008/013603;

PCT Application No. PCT/US2008/000141, filed Jan. 4, 2008, titled "Convective Warming Device with a Drape", and published Jul. 31, 2008 under Publication No. WO 2008/091486;

U.S. patent application Ser. No. 10/411,865, filed Apr. 10, 2003, titled "Patient Comfort Apparatus and System", and published on Oct. 16, 2003 under Publication No. US 2003/0195596, now U.S. Pat. No. 7,001,416;

U.S. patent application Ser. No. 10/508,319, filed Sep. 20, 2004, titled "Patient Comfort Apparatus and System", and published on Jun. 30, 2005 under Publication No. US 2005/0143796;

U.S. patent application Ser. No. 10/895,672, filed Jul. 21, 2004, titled "Perioperative Warming Device", now abandoned, published on Jan. 20, 2005, under Publication No. US 2005/0015127;

U.S. patent application Ser. No. 11/005,883, filed Dec. 7, 2004, titled "Warming Device with Varied Permeability", and published on Jun. 8, 2006 under Publication No. US 2006/0122671, now U.S. Pat. No. 7,226,454;

U.S. patent application Ser. No. 11/006,491, filed Dec. 7, 2004, titled "Warming Device", and published on Jun. 8, 2006 under Publication No. US 2006/0122672, now U.S. Pat. No. 7,364,584;

U.S. patent application Ser. No. 11/057,396, filed Feb. 11, 2005, titled "Perioperative Warming Device", and published on Aug. 17, 2006 under Publication No. US2006/0184215, now U.S. Pat. No. 7,276,076;

U.S. patent application Ser. No. 11/057,397, filed Feb. 11, 2005, titled "Thermal Blanket for Warming the Limbs", and published on Aug. 17, 2006 under Publication. No. US 2006/0184216;

U.S. patent application Ser. No. 11/057,403, filed Feb. 11, 2005, titled "Warming Device for Perioperative Use", and published on Aug. 17, 2006 under Publication No. US 2006/0184217;

U.S. patent application Ser. No. 11/057,404, filed Feb. 11, 2005, titled "Clinical Garment for Comfort Warming and Prewarming", and published on Aug. 17, 2006 under Publication No US 2006/0184218, now U.S. Pat. No. 7,470,280;

U.S. patent application Ser. No. 11/260,706, filed Oct. 27, 2005, titled "Patient Comfort Apparatus and System", and published on Mar. 9, 2006 under Publication No. US 2005/0052853;

U.S. patent application Ser. No. 11/363,136, filed Feb. 27, 2006, titled "Forced Air Warming Unit", and published on Jul. 6, 2006 under Publication No. US 2006/0147320;

U.S. patent application Ser. No. 11/583,432, filed Oct. 19, 2006, titled "Multifunction Warming Device for Perioperative Use", and published on Apr. 26, 2007 under Publication No. US 2007/0093882;

U.S. patent application Ser. No. 11/583,477, filed Oct. 19, 2006, titled "Multifunction Warming Device with Provision for Being Secured", and published on Apr. 26, 2007 under Publication No. US 2007/0093883;

U.S. patent application Ser. No. 11/583,480, filed Oct. 19, 2006, titled "Multifunction Warming Device with Provision for Warming Hands", and published on Apr. 26, 2007 under Publication No. US 2007/0093884;

U.S. patent application Ser. No. 11/583,481, filed Oct. 19, 200 "Multifunction Warming Device with an Upper Body Convective Apparatus", and published on Apr. 26, 2007 under Publication No. US 2007/0093885;

U.S. patent application Ser. No. 11/656,777, filed Jan. 23, 2007, titled "Convective Warming Device With a Drape", and published on Jul. 24, 2008 under Publication No. US 2008/0177361;

U.S. patent application Ser. No. 11/704,547, filed Feb. 9, 2007, titled "A Forced Air Warming Unit";

U.S. patent application Ser. No. 11/801,292, filed May 9, 2007, titled "Warming Device with Varied Permeability", and published on Oct. 11, 2007 under Publication No. US 2007/023939;

U.S. patent application Ser. No. 11/899,872, filed Sep. 7, 2007, titled "Perioperative Warming Method", and published on Jan. 31, 2008 under Publication No. US 2008/0027522;

U.S. patent application Ser. No. 11/899,928, filed Sep. 7, 2007, titled "Perioperative Warming Device", and published on Jan. 31, 2008 under Publication No. US 2008/0027521;

U.S. patent application Ser. No. 12/011,699, filed Jan. 1, 2008, titled "Warming Device" and published on Jun. 11, 2009 under Publication No. US 2009/0149931;

U.S. patent application Ser. No. 12/386,243, filed Apr. 15, 2009, titled "Warming Device with Provisions for Deploying Elements of an Upper Body Convective Apparatus and for Deploying the Lower Portion of the Warming Device" and published on Sep. 10, 2009 under Publication No. US 2009/0228083; and U.S. patent application Ser. No. 12/653,825, filed Dec. 21, 2009, titled "Warming Device Constructions with a Poncho-Type Patient Gown".

BACKGROUND

A warming device that may be used perioperatively includes a clinical garment and convective apparatus with multiple separately-inflatable sections supported on the inside of the garment, each section adapted to enable a particular mode of warming.

Convective devices that transfer heat to a human body are known. For example, there are devices that receive a stream of warmed pressurized air, inflate in response to the pressurized air, distribute it within a pneumatic structure, and emit the warmed air onto a body. These devices are typically called "thermal blankets", "convective thermal blankets" or "covers". Arizant Healthcare Inc., the assignee of this application, makes and sells such thermal blankets under the BAIR HUGGER® brand. One such device is the Model 522 Upper Body Blanket.

Use of the term "convective" to denote the transfer of heat between a warming device and a body refers to the principal mode of heat transfer, it being understood that heat may at the same time be transferred between a convective warming device and a body by conduction and radiation, although not to the degree of convection.

Convective warming has been used with increasing frequency to prevent or mitigate hypothermia during medical treatment. However, with the expansion of convective warming to treat core body cooling, it becomes apparent that it has manifold medical uses.

For example, a recent invention disclosed in the referenced Publication No. WO 2003/086500 adapts a clinical garment such as a robe or gown to receive a convective warming device in order to warm a person wearing the garment in a clinical setting for comfort and mobility of the person. Arizant Healthcare Inc., the assignee of this application, makes and sells such warming devices under the BAIR PAWS® brand. These devices are intended to warm patients prior to surgery, and there is a need to further adapt such a combination for use perioperatively.

The term "perioperative" is defined in the *PDR Medical Dictionary*, Second Edition, (Medical Economics Company, 2000), as "around the time of operation." The perioperative period is characterized by a sequence including the time preceding an operation when a patient is being prepared for surgery ("the preoperative period"), followed by the time spent in surgery ("the intraoperative period"), and by the time following an operation when the patient is closely monitored for complications while recovering from the effects of anesthesia ("the postoperative period").

According to Mahoney et al. (Maintaining intraoperative normothermia: A meta-analysis of outcomes with costs. *AANA Journal.* 4/99; 67, 2:155-164.), therapeutic warming is employed during at least the intraoperative period in order to prevent or mitigate hypothermia. In fact, it is increasingly manifest that maintenance of normothermia perioperatively enhances the prospects for a quick, successful recovery from surgery. The effectiveness of therapeutic warming depends upon delivery of enough heat to a patient's body to raise the patient's core body temperature to, or maintain it within, a narrow range, typically around 37° C. This range is called "normothermic" and a body with a core temperature in this range is at "normothermia." Hypothermia occurs when the core body temperature falls below 36° C.; mild hypothermia occurs when core body temperature is in the range of 34° C. to 36° C. Therefore, "perioperative therapeutic warming" is warming therapy capable of being delivered during one or more of the perioperative periods for the prevention or treatment of hypothermia.

Therapeutic warming is contrasted with "comfort warming" which is intended to maintain or enhance a patient's sense of "thermal comfort". Of course, therapeutic warming may also comfort a patient by alleviating shivering or a feeling of being cold, but this is a secondary or ancillary effect. And conversely, there may be a secondary or ancillary therapeutic effect derived from the application of thermal comfort treatments such as the relief of patient anxiety. Thermal comfort is a subjective notion; however, the environmental conditions necessary to produce a sense of thermal comfort in a population of human beings are known and well tabulated. For example, Fanger (*Thermal Comfort: Analysis and Applications of Environmental Engineering*. Danish Technical press, Copenhagen, 1970) defines thermal comfort as "that condition of mind which expresses satisfaction with the thermal environment." Even when a patient is normothermic, less than ideal environmental conditions can result in acute feelings of discomfort. Under normothermic conditions, thermal comfort is largely determined with reference to skin temperature, not core body temperature. Comfort warming is warming applied to a patient to alleviate the patient's sense of thermal discomfort.

Therapeutic warming may be indicated during any one or more of the perioperative periods. For example, for a short operation in a surgery with no warming equipment available, a person may be warmed preoperatively in a preparation area to raise mean body temperature to a level higher than normal in order to store enough thermal energy to maintain normothermia, without heating, intraoperatively. After surgery, it may be necessary to apply therapeutic warming in a recovery area to raise the core temperature to normothermia and maintain it there for a period of time while anesthesia wears off. Alternatively, for a long surgery in an arena with heating equipment available, a person may be warmed for comfort before surgery and warmed therapeutically during and after surgery.

Thermal blankets are typically used for therapeutic heating. An example is found in U.S. Pat. No. 6,524,332, "System and Method for Warming a Person to Prevent or Treat Hypothermia", commonly owned with this application. Thermal blanket designs have converged on a lightweight inflatable structure made of a flexible material which distributes warmed pressurized air over or against a permeable blanket surface that faces some portion of a patient's body and emits the distributed heated air through small apertures or interstices in the surface.

Thermal blanket design has been adapted for comfort warming by convective means such as those described in the referenced U.S. Patent Applications, and the referenced Publication No. WO 03/086500.

When delivered by convective devices, therapeutic warming is distinguished from comfort warming by intended effects and by the parameters of heat delivery that produce those effects. In this regard, a convective warming system typically includes a source of warmed pressurized air (also called a heater/blower unit, a forced air warming unit, a heater unit, etc.), a convective device such as a thermal blanket (which is, typically, inflatable), and a flexible conduit or air hose connecting the heater/blower unit with the thermal blanket. Use of such a system for a particular type of warming requires delivery of warmed air through a convective device at parametric values that achieve a particular objective. For example, for comfort warming, the temperature at the hose end, prior to the air entering the pneumatic convective device, may range from ambient to 42° C. (WO 03/086500 at page 11, lines 24-26). The conditions by which a convective device produces thermal comfort in normothermic individuals at steady state are significantly different from those necessary to treat hypothermia. Typically the conditions for thermal comfort are met in a system with a relatively low capacity heater/blower unit, while those in a therapeutic warming system are achieved with a relatively high capacity heater/blower unit. The different capacities have led to use of air hoses with different capacities, with those delivering air flow for thermal comfort typically having smaller diameters than those serving a therapeutic warming requirement. The result is a divergence of designs leading to installation of different air delivery infrastructures for therapeutic and comfort warming.

Health care cost is an issue of high importance. The cost of warming perioperatively by convection is directly related to the number of perioperative periods in which a person is warmed; the cost increases when different convective warming apparatus are used in different periods to accomplish different goals. For example, when comfort and mobility are objectives of warming a person during the preoperative period and therapy is the objective of warming during one or more of the intraoperative and postoperative periods, it is presently necessary to use different convective warming configurations. Manifestly, if one convectively-operating warming device could be used or adapted to be used perioperatively, significant savings in thermal care could be realized.

SUMMARY

In one aspect, a warming device capable of being used perioperatively includes a clinical garment having an inside surface supporting a convective apparatus with multiple separately inflatable sections. At least one section is adapted for comfort warming and at least another section is adapted for therapeutic warming.

In another aspect, a warming device that may be used perioperatively includes a clinical garment and interleaved convective apparatus in an integrated structure attached to the inside of the garment.

BRIEF DESCRIPTION OF THE DRAWINGS

FIGS. 4A and 4B are magnified partial sectional drawings illustrating construction of the convective apparatus.

SPECIFICATION

A warming device that may be used perioperatively is constituted of a clinical garment and a convective apparatus with multiple sections supported on an inside surface of the garment. In this regard, a "clinical garment" is a garment that is typically used to temporarily clothe a patient in a clinical setting. Such garments include hospital gowns, robes, bibs and other equivalents. The clinical setting may be a medical or dental office or clinic, a hospital, or any facility or institution that provides medical or dental treatment to patients. The convective apparatus has multiple sections, preferably two separate sections. Each section may receive and distribute at least one stream of warmed pressurized air in a pneumatic structure and emit the air through at least one permeable surface to thereby convectively warm a person wearing the clinical garment. One section is adapted for comfort warming by convection, the other for therapeutic warming by convection.

In one aspect, a warming device capable of perioperative use may be worn on a person where it receives a first stream of warmed pressurized air in one section of the convective apparatus, distributes the pressurized air within the one section, and emits the air through a permeable surface of the one section to convectively warm the person's body for comfort. In another aspect, a warming device capable of perioperative use may be worn on a person where it receives a second stream of warmed pressurized air in the other section of the convective apparatus, distributes the pressurized air within the other section, and emits the air through a permeable surface of the other section to convectively warm the person's body for therapy. Preferably, the permeable surfaces are respective sections or regions of the same surface. Further, although not necessary to the practice of this warming device, the permeable surfaces may have differing or varied permeabilities in order to optimize the effects produced by the sections of the convective apparatus.

In the warming device illustrated and discussed below, each of the sections of the convective apparatus is inflatable. That is, the structure of each section, flaccid when not in use, tautens when receiving a stream of pressurized air.

Figure 1:
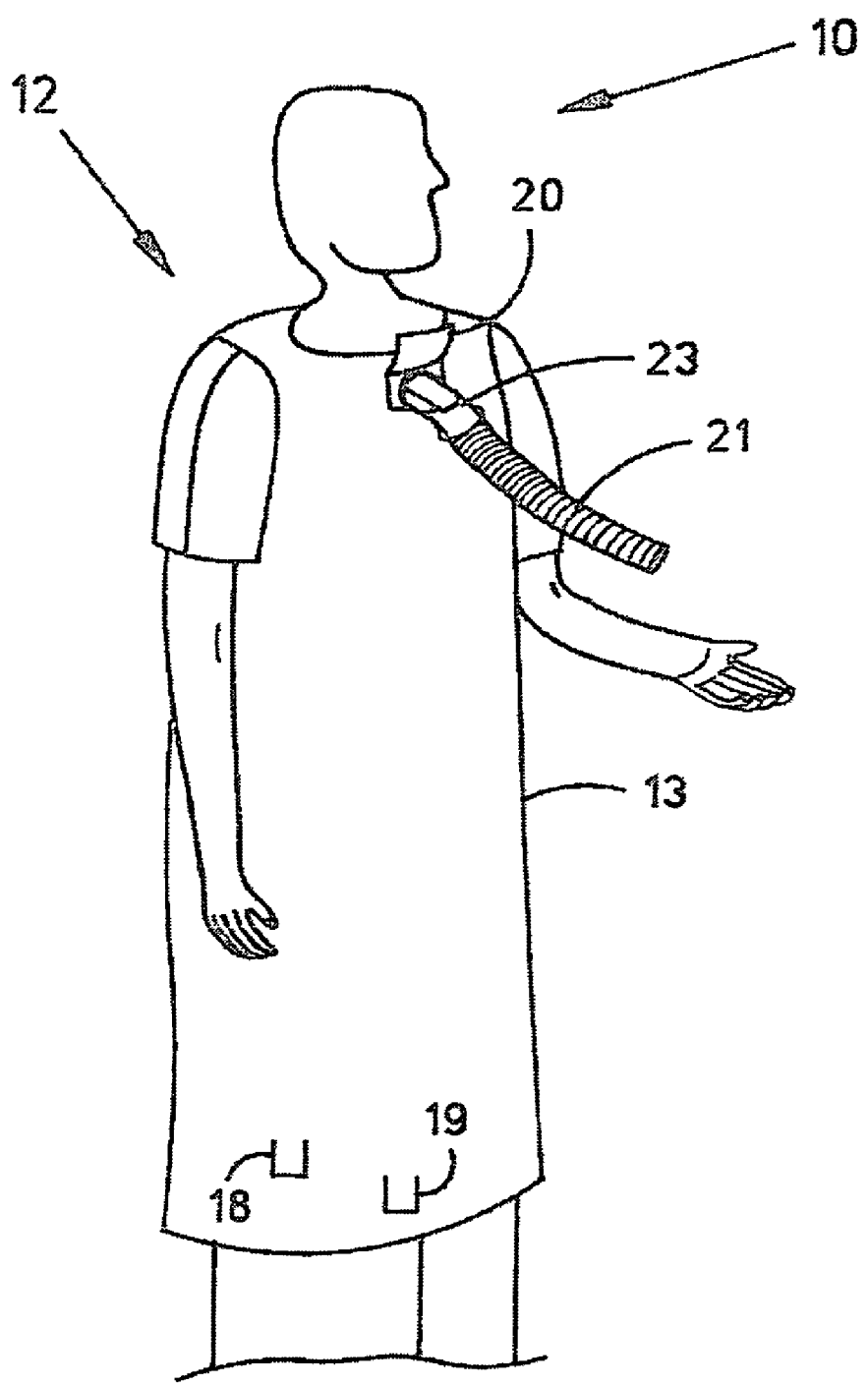
FIG. 1 is an illustration of a person wearing a warming device constituted of a clinical garment and a convective apparatus with multiple sections mounted to the inside of the garment.

Refer now to FIG. 1 in which a person 10 wearing a warming device 12 that may be used perioperatively is shown. The warming device 12 is constituted of a clinical garment 13 and a convective apparatus (not shown) with multiple sections that is supported on an inside surface of the clinical garment 13. The convective apparatus has for example two separate sections with inlet ports through which the sections may receive warmed pressurized air from a heater/blower unit (not seen). Each inlet port is accessible through an aperture in the clinical garment 13. The aperture may be open, or it may be closed as by a flap, or perforations, or a moveable or removable section of the clinical garment 13. An inlet port may also be accessed by releasing and folding a portion of the clinical garment 13 as illustrated in FIG. 1 of US Publication 2006/0122671A1. For example inlet ports may be accessed through apertures covered by flaps 18, 19, and 20 in the clinical garment. This latter form of access is illustrated in FIG. 1 where an air hose 21 with a nozzle 23 is received in an inlet port of one section of the convective apparatus. In this case, the flap 20 in the clinical garment 13 comprises a portion of the front of the clinical garment 13 that may be moved away from the garment.

Convective apparatus such as thermal blankets have been specifically designed for particular uses. For example, a full body thermal blanket is adapted to lie upon the person and to extend longitudinally along the body of the person in order to cover substantially the person's entire body, from near the ankles or feet up to the neck. A lower body thermal blanket is adapted to lie upon the person and to extend longitudinally along the body of a person in order to cover the person's lower body, from near the ankles or feet up to the waist or pelvis of the person. An upper body thermal blanket has a bow-tie shape that is adapted to lie upon and extend transversely across the upper body of a person in order to cover the person's chest and extended arms. When fed a stream of warmed pressurized air, each of these thermal blankets inflates and distributes the air within itself. The pressurized air flows through apertures on a permeable surface of the thermal blanket which faces the person. These thermal blankets may have one, two, or more inlet ports through which an air hose provides warmed pressurized air from a heater/blower unit. The construction of thermal blankets is well understood. Examples of specific constructions are given in U.S. Pat. No. 5,620,482, U.S. Pat. No. 5,443,488, U.S. Pat. No. 5,360,439, and U.S. Pat. No. 5,304,213. See also U.S. Pat. No. 5,974,605.

Typically, convective warming products are designed to provide a single mode of warming. Each of the thermal blankets described above is designed for therapeutic warming. The devices described in publication WO 03/086500 are designed for comfort warming. In contrast, the warming device described in this specification may provide either therapeutic warming or comfort warming, depending on the need. One section of the convective apparatus is constructed to receive air at low flow rates in order to provide comfort heating at steady state. Another section is constructed to receive air at higher flow rates in order to provide therapeutic heating at steady state.

Figure 2A:
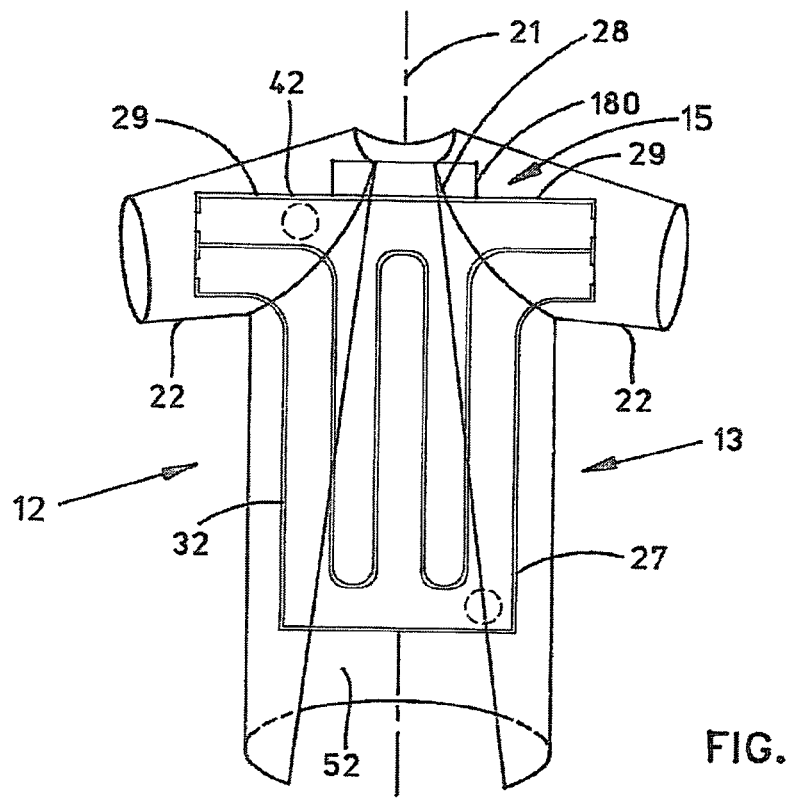
FIG. 2A is a back elevation view of the warming device.
Figure 2B:
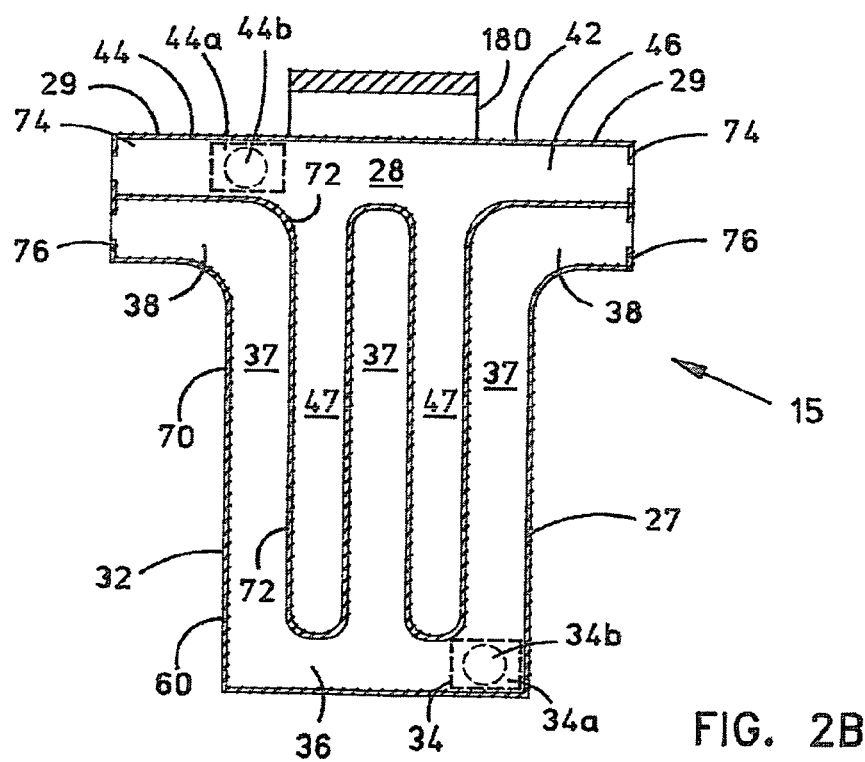
FIG. 2B is a plan view of a convective apparatus with multiple sections in the warming device of FIG. 2A.

A convective apparatus 15 with multiple sections is illustrated in FIGS. 2A and 2B. In FIG. 2A the convective apparatus 15 is shown disposed inside the outline of the clinical garment 13; in FIG. 2B, the convective apparatus 15 is shown in plan view looking toward a permeable surface of the convective apparatus 15. The convective apparatus 15 has a "Tee" shape with a thick base 27 and an elongate top 28 which is perpendicular to the base 27. The elongate top 28 extends transversely across a longitudinal axis 21 of the clinical garment 13, between and at least partly into the sleeves 22 of the clinical garment 13. The base 27 is substantially centered on the longitudinal axis 21. The elongate top 28 has portions 29 on either side of the base 27. Each of the portions 29 protrudes at least part way into a respective sleeve 22 of the clinical garment 13.

The convective apparatus 15 has multiple sections. A "section" of the convective apparatus 15 is a portion or division of the convective apparatus 15 that may be inflated and operated separately from any other section of the convective apparatus 15. For example, the convective apparatus 15 has a section 32 and a section 42. The section 32 may be inflated and operated separately from the section 42, and the section 42 may be inflated and operated separately from the section 32. The section 32 has an inlet port 34, an elongate transverse part 36, and a plurality of elongate parts 37 that connect perpendicularly to the transverse part 36. Each of the two outermost elongate parts 37 transitions through an outward 90° bend to a sleeve portion 38. Each sleeve portion 38 is in a respective portion 29 of the convective apparatus 15. Although one inlet port 34 is illustrated in the section 32, one or more additional inlet ports may be provided for convenience. Unused inlet ports are sealed or closed by known means to prevent air escaping therethrough. Preferably the inlet port 34 is provided through the side of the convective apparatus 15 which is not visible in this figure; it may also be provided through an edge of the convective apparatus 15. The inlet port 34 may comprise a collar 34a of stiff material with an opening 34b to receive the nozzle of an air hose, or it may comprise a sleeve of material, or any other equivalent structure. The space in the transverse part 36 is in fluid communication with the spaces in the elongate parts 37 so that pressurized air flowing through an inlet port into the transverse part 36 flows also into the elongate parts 37, thereby inflating the section 32. The surface of the section 32 which is visible in FIG. 2, including the surfaces of the transverse part 36 and the elongate parts 37, is permeable, permitting pressurized air that is flowing into and inflating the section 32 to be expelled toward the interior of the clinical garment 13.

The section 42 has an inlet port 44, an elongate transverse part 46, and a plurality of elongate parts 47 that connect perpendicularly to the transverse part 46. The elongate transverse part 46 is parallel and adjacent to the sleeve portions 38 of the section 32. The end portions of the elongate part 46 are in respective portions 29 of the convective apparatus 15. The elongate parts 47 of the section 42 are interleaved with the elongate parts 37 of the section 32, thereby forming an integrated convective apparatus 15 with dual sections. Although one inlet port 44 is illustrated in the section 42, one or more additional inlet ports may be provided for convenience. Unused inlet ports are sealed or closed by known means to prevent air escaping therethrough. Preferably the inlet port 44 is provided through the side of the convective apparatus 15 which is not visible in this figure; it may also be provided through an edge of the convective apparatus 15. The inlet port 44 may comprise a collar 44a of stiff material with an opening 44b to receive the nozzle of an air hose, or it may comprise a sleeve of material, or any other equivalent structure. The space in the transverse part 46 is in fluid communication with the spaces in the elongate parts 47 so that pressurized air flowing through an inlet port into the transverse part 46 flows also into the elongate parts 47, thereby inflating the section 42. The surface of the section 42 which is visible in FIG. 2, including the surfaces of the transverse part 46 and the elongate parts 47, is permeable, permitting pressurized air that is flowing into and inflating the section 42 to be expelled toward the interior of the clinical garment 13.

The inlet port 34 of the section 32 has a smaller opening 34b than the opening 44b through the inlet port 44 of the section 42. Consequently, the inlet port 34 accepts an air hose nozzle with a smaller diameter than the air hose nozzle diameter accepted by the inlet port 44. The smaller nozzle diameter signifies a comfort warming air supply with an air hose having a smaller diameter than the air hose of a therapeutic warming air supply. Further, the smaller air hose may be coupled to a heater/blower unit with a smaller capacity than that of the heater/blower unit of the therapeutic warming air supply. The smaller-diameter, smaller-capacity comfort warming air supply ensures that the section 32 operates in response to a heater/blower unit designed for comfort warming while the larger-diameter, higher-capacity therapeutic air supply ensures that the section 42 operates in response to a heater/blower unit designed for therapeutic warming.

Figure 3A:
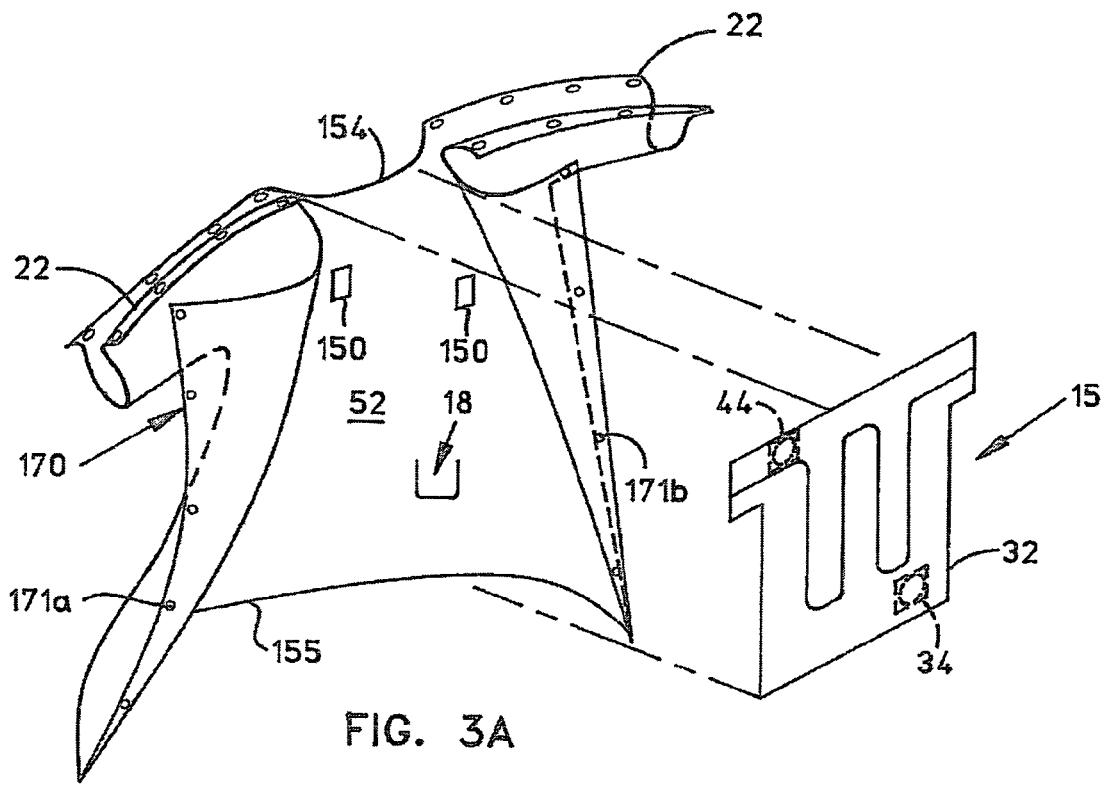
FIGS. 3A and 3B illustrate progressive stages of assembly of a warming device.
Figure 3B:
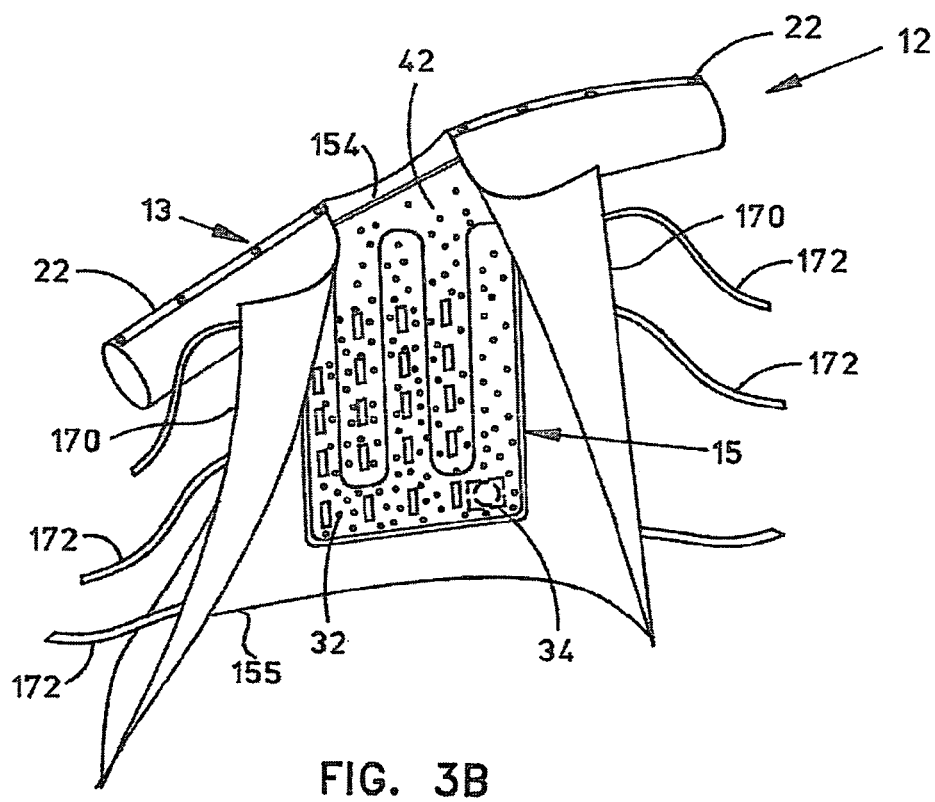

FIGS. 3A and 3B illustrate assembly of a perioperative warming device constituted of the clinical garment 13 and the convective apparatus 15 with multiple sections. The convective apparatus 15 is adapted to be attached to, received on, supported on or constructed on the inside surface 52 of the clinical garment 13. The clinical garment 13 has at least one flap 18 through which an inlet port of one section may be accessed. For example, the flap 18 provides access to the inlet port 34 for receiving and retaining the nozzle of an air hose through which warmed pressurized air may be provided at a temperature and a capacity (in ft$^3$ per minute) to provide comfort warming for a person wearing the clinical garment 13.

Refer to FIGS. 2B, 3B, and 4 for an understanding of how the convective apparatus 15 may be constructed by joining two sheets of material, one permeable to permit warmed pressurized air to be emitted through the sheet, the other impermeable. With reference to FIGS. 2B and 3B, the impermeable sheet faces the clinical garment 13, while the permeable sheet faces the interior of the clinical garment 13. The convective apparatus 15 may be constructed as a separate piece and then attached to the inside surface 52 of the clinical garment 13 with the impermeable sheet against the inside surface 52, or it may be constructed integrally with the clinical garment by using a portion of the clinical garment itself as one of the sheets of the convective device. For example, with reference to FIGS. 2B and 4 two sheets 114 and 116 of flexible material are joined by a single substantially continuous seal 70 along the periphery of the convective apparatus 15, and also by a continuous seal 72 that separates the sections of the convective apparatus and defines the parts of each section. The seal 70 is interrupted at the ends of the transverse part 46 to provide vents 74 in the peripheral edge of the convective apparatus 15 through which warmed pressurized air can flow from the convective apparatus 15 into the sleeves 22 for warming the arms during therapeutic warming. Similarly, the seal 70 is interrupted at the ends of the arm portions 38 to provide vents 74 in the peripheral edge of the convective apparatus 15 through which warmed pressurized air can flow from the convective apparatus 15 into the sleeves 22 for warming the arms during comfort warming. The sheets may be further joined at multiple stake points within the periphery. Depending upon the materials selected, seals and stake points may be made for example by sewing, gluing, heating, or ultrasonically bonding the sheets along the seals, or by combinations thereof, or by any equivalent process.

Either or both of the sheets 114 and 116 may be a single sheet or may have a laminate structure. A laminate sheet structure may include a layer (114a, 116a) of extruded synthetic material lined with a layer (114b, 116b) of non-woven material. If the permeable sheet has a laminate structure, holes or apertures 132 are formed through both layers 114a, 114b of the sheet 114 to provide a permeable surface through which warmed pressurized air can be emitted toward the interior of the clinical garment 13. In FIG. 4A, the sheets 114 and 116 are oriented to have the extruded layers (114a and 116a) facing, and the seals 70, 72 are formed by a gluing process or by a heating or ultrasonic process acting through one of the layers of non-woven material. Once constructed, the convective apparatus 15 may be attached to the inside surface 52 of the clinical garment by mechanisms 150.

In FIG. 4B, the sheet 114 may be a laminate structure as described above. If the clinical garment 13 is a woven cloth, such as cotton, or a non-woven such as spunbond-meltblown-spunbond material (SMS), the seals 70, 72 between the portion of the garment's inside surface 52 and the extruded layer of the laminate sheet may be formed by a gluing, a heating, or an ultrasonic process acting between the inside surface and the sheet 114.

Another construction of the convective apparatus 15 may use a single sheet of permeable material in which the apertures are interstices in the material structure. For example with reference to either FIG. 4A or FIG. 4B, the impermeable layer 114a may be eliminated on the condition that the layer 114b be a permeable material capable of being sealed to the impermeable layer 116a or the woven cloth of the clinical garment.

Yet another alternative construction of the convective apparatus 15 is to construct the clinical garment 13 of a laminate sheet 116 and seal an apertured laminate sheet 114 or a single permeable layer 114b of woven or non-woven material thereto.

In yet another construction, the convective device may be constituted of an impermeable layer sealed around its periphery to the outside surface of the clinical garment so that the pneumatic structure is disposed on the outside of the clinical garment. In this case apertures are provided through the portion of the clinical garment beneath the impermeable layer.

Of course the sections of the convective device may be fabricated separately and placed on the inside surface 52 in the interleaved relationship shown in FIGS. 2A and 2B.

Examples of non-woven material include any one or more of polyester, cotton, rayon, polypropylene, and wood pulp. Examples of extruded synthetic material include polypropylene, polyesters, and polyurethanes. Polyolefin plastics, including polyethylene, may provide the best results in terms of manufacturability since both woven and extruded materials may be made from them. Examples of attachment materials and mechanisms 150 by which the convective apparatus 15 as presented in FIG. 4A can be attached to the inside surface 52 include two-sided adhesive, hook and loop, sewing, snaps, heat, ultrasonic, rivets, and any and all equivalents thereof.

As best seen in FIGS. 3A and 3B, the clinical garment 13 may be a standard gown, a modified gown or a special purpose gown. The gown may have a rear opening, a front opening, a side opening or other suitable openings, such as a head opening in a poncho type gown. One type of gown shown in the figures has a rear opening. For example, in FIGS. 3A and 3B the gown 13 has a slit 170 that extends from the neck portion 154 to a hemline 155. A fastening means is provided to provide for ease in securing the gown to the patient as well as allowing for ease in adjusting the size of the gown to accommodate various different-sized wearers. FIG. 3A shows one method using hook and loop buttons 171a, 171b positioned along opposing sides of the slit 170a, 170b that can be brought together and fastened to hold the gown to the patient. Another method of attachment shown in FIG. 3B is a plurality of strings 172 positioned along opposing sides of the slit 170 that can be tied together to hold the gown to a patient. Other methods of attachments include hook and eye elements, double-sided adhesive, snaps, rivets, and any and all equivalents thereof.

The clinical garment 13 may include sleeves 22 that are sized and positioned for receiving a patient's arms. Two examples of such sleeves 22 are shown in the figures. In FIGS. 3A-3B the sleeve portions 175 are slit the entire length on the shoulder or top 177. This allows access to the upper body of the patient and the inlet port 44 and allows for opening and closing of the slit sleeves 22 in an adjustable fashion using buttons, snaps, repositionable adhesive, hook and eye elements, double-sided adhesive, hook and loop, rivets, and any and all equivalents thereof. The design shown in FIG. 3A also facilitates the preferred manufacture of the clinical garment 13 based on a body piece to which sleeve pieces are attached. Manifestly, the clinical garment may also be manufactured in one piece.

As best seen in FIGS. 2A and 2B, to secure the convective apparatus to a patient, a strip 180 of double sided adhesive is adhered to the transverse part 42. During use of the perioperative warming device 12, a release liner may be removed from a surface of the strip 180 facing the patient and adhered to the patient to prevent unintended movement of the convective apparatus 15 during warming.

Figure 5A:
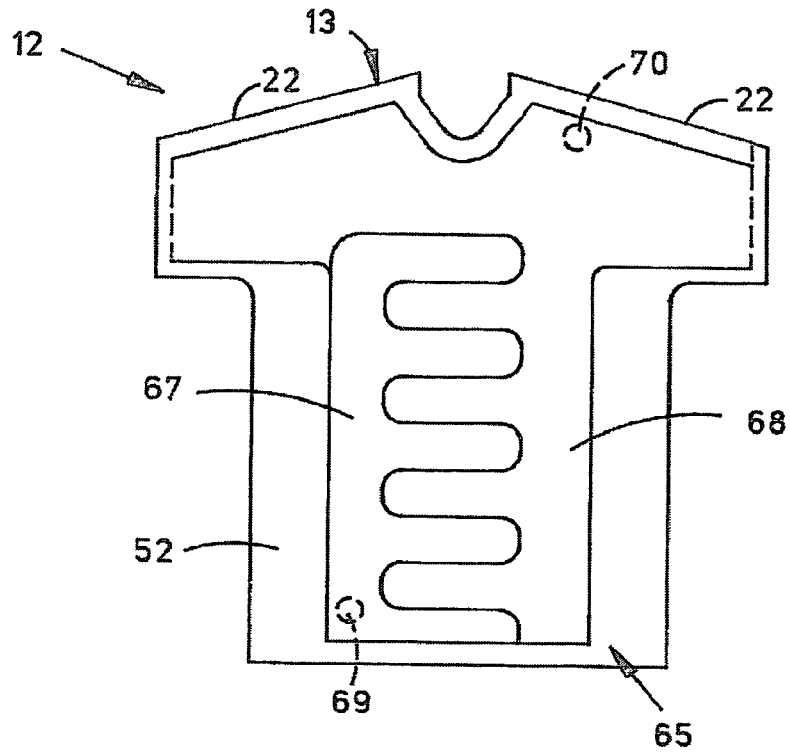
FIGS. 5A-5C are plan views of alternate configurations for a convective apparatus with multiple sections.
Figure 5B:
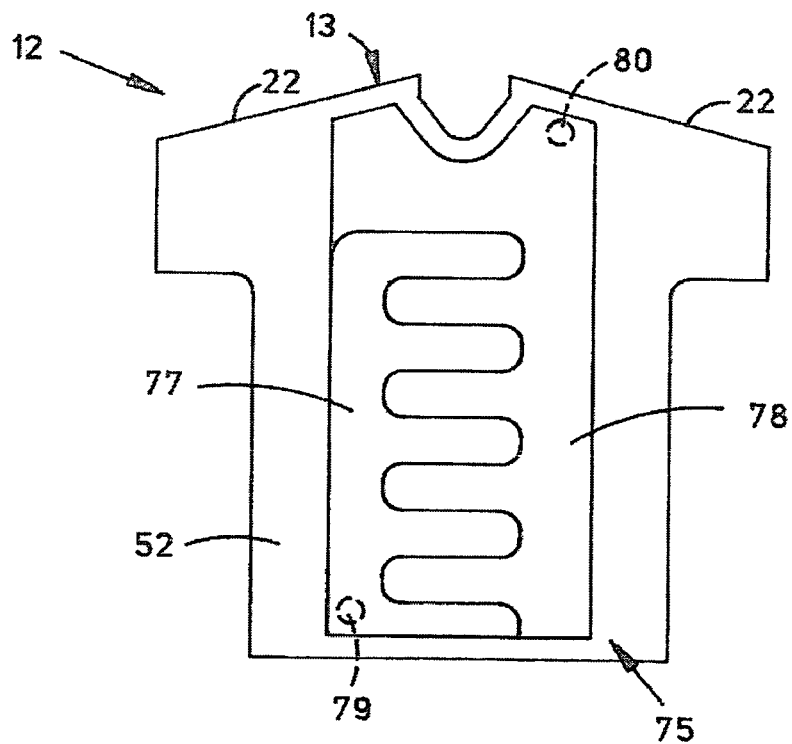
Figure 5C:
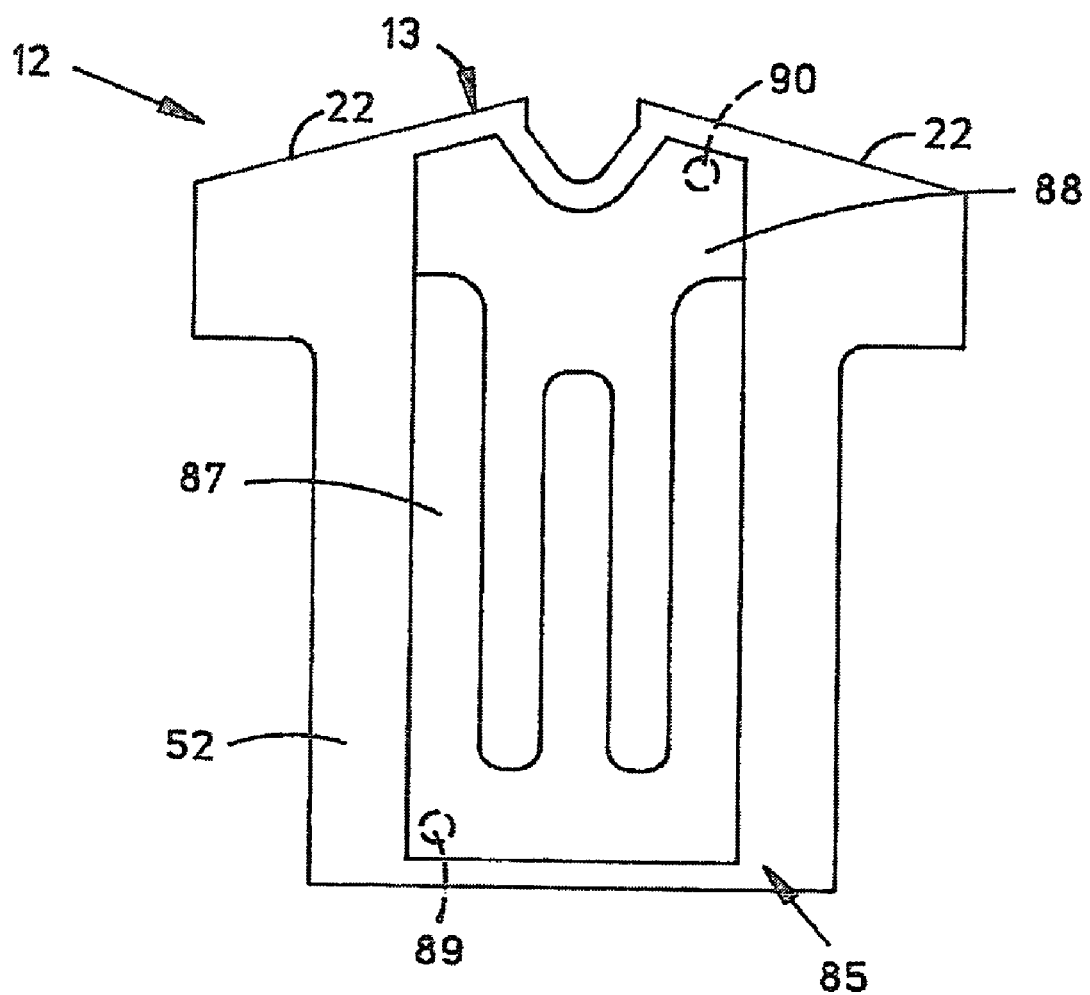

Other configurations of the convective apparatus with multiple sections may be more useful for particular applications or may be more amenable to particular manufacturing architectures and/or processes than the configurations shown and discussed above; FIGS. 5A-5C illustrate three alternative configurations. Each of these figures is a schematic illustration of a convective apparatus with multiple sections presented against an outline of the clinical garment 13. The view in each case is into the clinical toward the inside surface. Accordingly, the permeable surfaces of the sections of the convective devices are visible in each drawing.

In FIG. 5A, the warming device 12 includes the clinical garment 13 and a Tee-shaped convective device 65 with multiple sections is illustrated. For example, the convective device has two sections, a section 67 and a section 68. The section 67 may be inflated and operated separately from the section 68, and the section 68 may be inflated and operated separately from the section 67. The section 67 has an elongate comb-shaped outline, with the teeth of the comb oriented generally transversely across the inside surface 52. The section 67 has an inlet port 69 (accessible through the front of the clinical garment 13). The section 68 has a comb-shaped lower part, with the teeth of the comb oriented generally transversely across the inside surface 52 and interleaved with the teeth of the section 67. The section 68 also has a transverse part that extends between and at least partially into sleeves 22 of the clinical garment 13. The section 68 has an inlet port 70 (accessible through the front of the clinical garment 13). Preferably, the section 67 may be used for comfort warming by convection, while the section 68 may be used for therapeutic warming by convection. In this latter regard the larger pneumatic structure and larger area of the permeable surface of the section 68 afford a higher capacity in ft$^3$ per minute for warming than the section 67.

In FIG. 5B, the warming device 12 includes the clinical garment 13 and a convective device 75 with multiple sections is illustrated. For example, the convective device has two sections, a section 77 and a section 78. The section 77 may be inflated and operated separately from the section 78, and the section 78 may be inflated and operated separately from the section 77. The section 77 has an elongate comb-shaped outline, with the teeth of the comb oriented generally transversely across the inside surface 52. The section 77 has an inlet port 79 (accessible through the front of the clinical garment 13). The section 78 has a comb-shaped lower part, with the teeth of the comb oriented generally transversely across the inside surface 52 and interleaved with the teeth of the section 77. The section 78 also has a notched upper part that does not extend between the sleeves of the clinical garment 13. The section 78 has an inlet port 80 (accessible through the front of the clinical garment 13). Preferably, the section 77 may be used for comfort warming by convection, while the section 78 may be used for therapeutic warming by convection. In this latter regard the larger pneumatic structure and larger area of the permeable surface of the section 78 afford a higher capacity in ft$^3$ per minute for warming than the section 77.

In FIG. 5C, the warming device 12 includes the clinical garment 13 and a convective device 85 with multiple sections is illustrated. For example, the convective device has two sections, a section 87 and a section 88. The section 87 may be inflated and operated separately from the section 88, and the section 88 may be inflated and operated separately from the section 87. The section 87 has an upright comb-shaped outline, with the teeth of the comb oriented generally upwardly along the middle of the inside surface 52. The section 87 has an inlet port 89 (accessible through the front of the clinical garment 13). The section 88 has a comb-shaped part, with the teeth of the comb oriented generally downwardly along the inside surface 52 and interleaved with the teeth of the section 87. The section 88 also has a notched upper part that does not extend between the sleeves of the clinical garment 13. The section 88 has an inlet port 90 (accessible through the front of the clinical garment 13). Preferably, the section 87 may be used for comfort warming by convection, while the section 88 may be used for therapeutic warming by convection. In this latter regard the larger pneumatic structure and larger area of the permeable surface of the section 88 afford a higher capacity in ft$^3$ per minute for warming than the section 87.

Figure 6A:
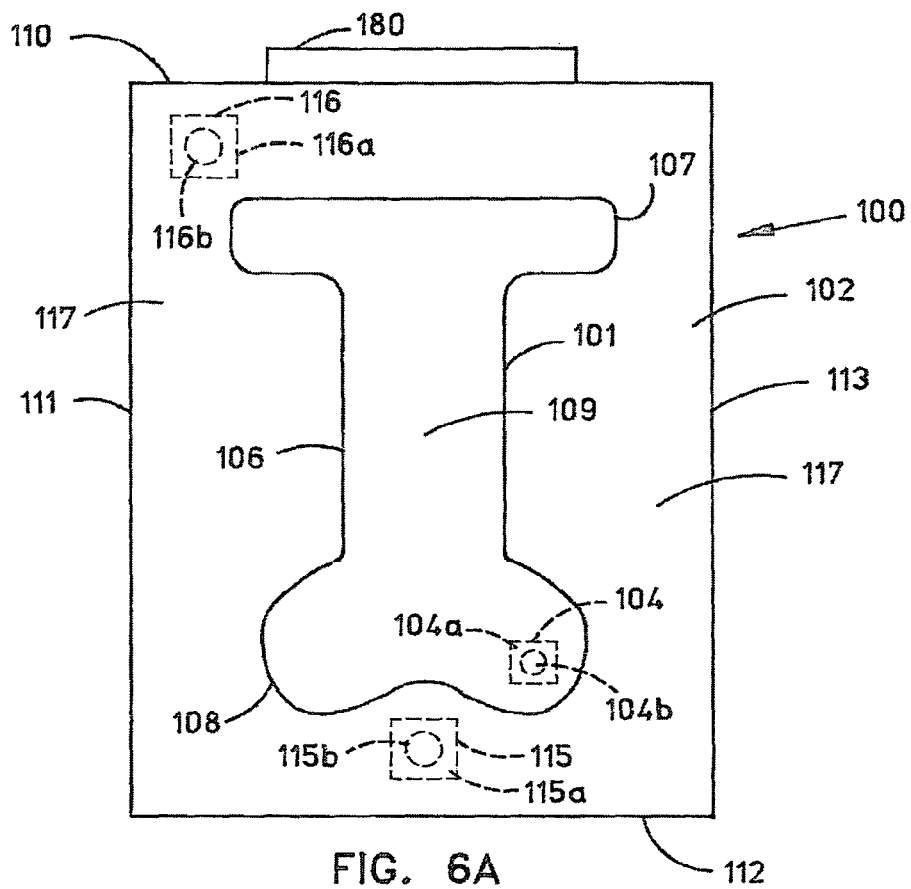
FIG. 6A is a plan view of another configuration for a convective apparatus with multiple sections.

A convective apparatus 100 with separately inflatable sections 101 and 102 is illustrated in FIG. 6A. In the convective apparatus shown in FIG. 6A, the section 101 has an inlet port 104, an elongate central part 106, and upper and lower transverse parts 107 and 108 that connect perpendicularly to the central part 106. The ends of the upper and lower transverse parts 107 and 108 are rounded, so that, in the plan view of FIG. 6A, the section 101 has a "dog bone" shape. Although one inlet port 104 is illustrated in the section 101, one or more additional inlet ports may be provided for convenience. Unused inlet ports are sealed or closed by known means to prevent air escaping therethrough. Preferably the inlet port 104 is provided through the surface of the convective apparatus 100 which is not visible in this figure. The inlet port 104 may comprise a collar 104a of stiff material with an opening 104b to receive the nozzle of an air hose, or it may comprise a sleeve of material, or any other equivalent structure. The space in the central part 106 is in fluid communication with the spaces in the transverse parts 107 and 108 so that pressurized air flowing through the inlet port 104 flows throughout the parts 106-108, thereby inflating the first section 101. The surface 109 of the section 101 which is visible in FIG. 6A, including the surfaces of the parts 106-108, is permeable, permitting pressurized air that is flowing into and inflating the first section 101 to be expelled toward the interior of the clinical garment 13. In some aspects of the first section 101, the permeability of the surfaces of the parts 106-108 may vary in order to reduce or eliminate variances in temperature of air expelled through the permeable surface 109 of the section 101.

As seen in FIG. 6A, the second section 102 has a quadrilateral outline with upper and lower edges 110 and 112 and side edges 111 and 113. The second section 102 generally forms an outline that frames the first section 101. Two inlet ports 115 and 116 are illustrated in the second section 102, although additional inlet ports may be provided for convenience. Preferably, the two inlet ports 115, 116 are well separated, with the inlet port 115 positioned between the lower edge 112 and the lower transverse part 108 of the first section 101, and the inlet port 116 positioned near the upper edge 110, above the upper transverse part 107 of the first section 101. Preferably the inlet ports 115 and 116 are provided through the surface of the convective apparatus 100 which is not visible in FIG. 6A, although either or both may also be provided through an edge of the convective apparatus 100. The inlet port 115 may comprise a collar 115a of stiff material with an opening 115b to receive the nozzle of an air hose, or it may comprise a sleeve of material, or any other equivalent structure. Similarly, the inlet port 116 may comprise a collar 116a of stiff material with an opening 116b to receive the nozzle of an air hose, or it may comprise a sleeve of material, or any other equivalent structure. Pressurized air flowing through either of the inlet ports 115, 116 inflates the second section 102. Unused inlet ports may be sealed or closed by known means to prevent air escaping therethrough. For example unused inlet ports may be closed by plugs such as are described in the assignee's U.S. Pat. No. 6,309,408. The surface 117 of the section 102 which is visible in FIG. 6A is permeable, permitting pressurized air that is flowing into and inflating the section 102 to be expelled toward the interior of the clinical garment 13.

In the convective apparatus 100 shown in FIG. 6A, the inlet port 104 of the first section 101 has a smaller opening 104b than the openings 115b and 116b through the inlet ports 115 and 116 of the second section 102. The openings 115b and 116b of the second section 102 are of equal size. Consequently, the inlet port 104 accepts an air hose nozzle with a smaller diameter than the air hose nozzle diameter accepted by the inlet ports 115 and 116. The smaller nozzle diameter signifies a comfort warming air supply with an air hose having a smaller diameter than the air hose of a therapeutic warming air supply. That is to say, the smaller air hose may be coupled to a heater/blower unit with a smaller capacity than that of the heater/blower unit of a therapeutic warming air supply, which can be connected to either of the inlet ports 115, 116 of the second section 102. The provision of an inlet port 104 dimensioned for a smaller-diameter hose enables the first section 101 to operate in response to a lower capacity heater/blower unit designed for comfort warming. The provision of inlet ports 115 and 116 dimensioned for a larger-diameter hose enables the second section 102 to operate in response to a higher capacity heater/blower unit designed for therapeutic warming. The first section 101 is thus constructed for comfort warming and the second section 102 for therapeutic warming.

Figure 6B:
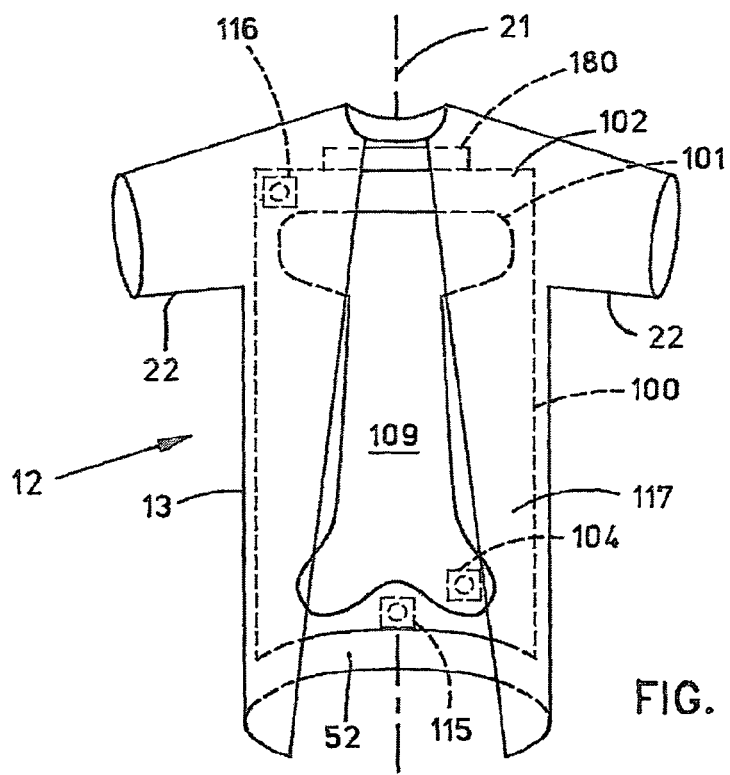
FIG. 6B is a back elevation view of the warming device with the convective apparatus of FIG. 6A mounted to the inside of the clinical garment.

FIG. 6B shows a warming device 12 for perioperative use assembled from the clinical garment 13 and the convective apparatus 100 with separately inflatable sections 101 and 102 illustrated in FIG. 6A. In the warming device 12, convective apparatus 100 is supported on the inside surface 52 of the clinical garment 13 with the orientation seen in FIG. 6A. In FIG. 6B, the view is toward the permeable surfaces of the convective apparatus 100. As illustrated in FIG. 6B, the convective apparatus 100 with separately inflatable sections 101 and 102 for comfort and therapeutic warming is supported on the inside surface 52, disposed longitudinally of the clinical garment 13, with the longitudinal axis 21 and extending toward the hem 155. The convective device 100 has the construction illustrated in FIG. 6A with a first, dog-bone shaped section 101 to provide comfort warming and a second section 102 that frames the dog-bone shaped section 101 to provide therapeutic warming. An opening in the clinical garment 13 (such as the flap 18 in FIG. 1, or a slit, a perforation, or a void in the garment) provides access by which an air hose can connect to the inlet port 104 of the first section 101 of the convective device 100 to operate the first section 101 for comfort warming. Warmed, pressurized air flows into and inflates the first section 101, and exits through the permeable surface 109 of the first section 101, toward a patient. An opening in the clinical garment 13 (such as the flap 19 in FIG. 1, or a slit, a perforation, or a void in the garment) provides access through the garment 13 at a first location by which an air hose can connect to the inlet port 115 of the second section 102 to operate the second section for therapeutic warming. An opening in the clinical garment 13 (such as the flap 20 in FIG. 1, or a slit, a perforation, or a void in the garment) provides access through the garment 13 at a second location by which an air hose can connect to the inlet port 116 of the second section 102 to operate the second section for therapeutic warming. Warmed, pressurized air flows into and inflates the second section 102 by way of the inlet port 115 or the inlet port 116, and exits through the permeable surface 117 of the second section 102, toward a patient.

The convective apparatus 100 may be constructed separately from the clinical garment 13 or may be integrated into the construction of the clinical garment as described above.

As seen in FIGS. 6A and 6B, to secure the convective apparatus 100 to a patient, a strip 180 of double sided adhesive is adhered to the convective apparatus near or at the upper edge 110. During use of the perioperative warming device 12, a release liner may be removed from a surface of the strip 180 facing the patient and adhered to the patient to prevent unintended movement of the convective apparatus 100 during warming.

In use, a person may be warmed perioperatively using a warming device constituted of a clinical garment and a dual-section convective apparatus supported on an inside surface of the clinical garment by dressing a person with the clinical garment during the preoperative period, coupling a first section (the section 32 in FIG. 2B, or the section 101 in FIG. 6A, for example) of the convective apparatus to a source of warmed pressurized air for comfort warming, and convectively warming the person for comfort by way of the first section. To prepare for surgery, the first section is decoupled from the comfort warming source and the clinical garment is arranged to afford access to a surgical site. In preparation for surgery, the clinical garment may be left on the person, with its skirts rolled up to provide surgical access. Alternatively, the clinical garment may be removed to allow the convective apparatus to be positioned on the person to provide surgical access. In this latter case, the skirts, sleeves and other loose parts of the clinical garment may be rolled or folded onto the convective device. In yet another alternative, if the convective device is releasably attached to the inside surface of the clinical garment, the garment may be separated from the convective device during surgery and reattached later postoperatively. During surgery, the convective device may be secured to the person by means of the double sided adhesive and a second section of the convective apparatus (for example the section 42 in FIG. 2B) may be coupled to a source of warmed pressurized air for therapeutic warming, and the person may be convectively warmed for therapy by way of the second section. Following surgery, the convective apparatus is detached from the person (but only if secured to the person for surgery), the convective apparatus is reattached to the clinical garment (but only if detached therefrom for surgery), the person is again dressed with the clinical garment and either warmed for comfort or warmed for therapy.

Manifestly, the descriptions and illustrations in this specification are presented for an understanding of how to make and use an exemplary warming device. The only limitations on the scope of protection afforded the inventive principles presented are in the following claims

The invention claimed is:

1. A warming device, comprising:
a clinical garment with an inside surface;
a convective apparatus supported on the inside surface;
the convective apparatus including an inflatable dog-bone shaped section framed by an outline section.

2. The warming device of claim 1, wherein the outline section is an inflatable section.

3. The warming device of claim 2, wherein the dog-bone shaped and outline sections are separately inflatable and each includes a permeable surface facing the interior of the clinical garment and the dog-bone shaped section includes an inlet port, further including one of a flap, a slit, a perforation, or a void in the clinical garment that provides access to the inlet port of the dog-bone shaped section.

4. The warming device of claim 2, wherein the dog-bone shaped and outline sections are separately inflatable and each includes a permeable surface facing the interior of the clinical garment, the dog-bone shaped section includes an inlet port, and the outline section includes two inlet ports, further including one of a flap, a slit, a perforation, or a void in the clinical garment that provides access to an inlet port of the outline section.

5. The warming device of claim 2, wherein the dog-bone shaped and outline sections are separately inflatable and each includes a permeable surface facing the interior of the clinical garment, the dog-bone shaped section includes an inlet port, the outline section includes two inlet ports, and the inlet port of the dog-bone shaped section has a dimension to accept a warming hose nozzle of a first diameter and each inlet port of the outline section has dimensions to accept a warming hose nozzle of a second diameter larger than the first diameter, further including plugs closing inlet ports to prevent air escaping therethrough.

6. The warming device of claim 2, wherein the dog-bone shaped and outline sections are separately inflatable and each includes a permeable surface facing the interior of the clinical garment, the dog-bone shaped section includes an inlet port, and the inlet port is through a surface of the convective apparatus.

7. The warming device of claim 2, wherein the dog-bone shaped and outline sections are separately inflatable and each includes a permeable surface facing the interior of the clinical garment, the dog-bone shaped section includes an inlet port, and the inlet port comprises a collar of stiff material with an opening to receive the nozzle of an air hose.

8. The warming device of claim 2, wherein the dog-bone shaped and outline sections are separately inflatable and each includes a permeable surface facing the interior of the clinical garment, the dog-bone shaped section includes an inlet port, the outline section includes two inlet ports, and the inlet port of the dog-bone shaped section has a dimension to accept a warming hose nozzle of a first diameter, each inlet port of the outline section has dimensions to accept a warming hose nozzle of a second diameter larger than the first diameter, and each inlet port comprises a sleeve of material.

9. The warming device of claim 1, the clinical garment further including sleeves, in which a portion of at least one sleeve is separable from a corresponding portion of the sleeve.

10. The warming device of claim 9, further including means for releasably joining the sleeve portions.

11. The warming device of claim 9, wherein each sleeve has a slit along its entire length, on the top of the sleeve.

12. The warming device of claim 11, including one of buttons, snaps, repositionable adhesive, hook and eye elements, double-sided adhesive, hook and loop, and rivets for closing the slits.

13. The warming device of claim 1, including a strip of double-sided adhesive on the convective apparatus for securing the warming device to a person.

14. The warming device of claim 1, wherein the clinical garment is one of a hospital gown, a robe, and a bib.

15. The warming device of claim 1, wherein the clinical garment is a gown having one of a rear opening, a front opening, and a side opening.

16. The warming device of claim 1, wherein the clinical garment is a poncho type gown having a head opening.

* * * * *

UNITED STATES PATENT AND TRADEMARK OFFICE
CERTIFICATE OF CORRECTION

| | |
|---|---|
| PATENT NO. | : 8,257,415 B2 |
| APPLICATION NO. | : 13/200966 |
| DATED | : September 4, 2012 |
| INVENTOR(S) | : Carol J Panser |

It is certified that error appears in the above-identified patent and that said Letters Patent is hereby corrected as shown below:

Page 2, Column 2,
Under Other Publications, line 5, delete "www.portachil.com/, Dec. 3, 2022." and insert -- www.portachill.com/, Dec. 3, 2002. --, therefor.

Column 1,
Line 8, delete "7,846,192" and insert -- 7,846,192. --, therefor.

Column 2,
Line 5, delete "Publication." and insert -- Publication --, therefor.
Line 38, delete "200" and insert -- 2006, titled --, therefor.

Column 14,
Line 50, delete "claims" and insert -- claims. --, therefor.

Signed and Sealed this
Twenty-seventh Day of November, 2012

David J. Kappos
*Director of the United States Patent and Trademark Office*